(12) United States Patent
Capers et al.

(10) Patent No.: US 9,161,858 B2
(45) Date of Patent: Oct. 20, 2015

(54) GUIDE FOR TEAR-OFF EYEWEAR LENS STRIPS

(71) Applicants: Seth Jared Capers, Argyle, TX (US); Seth Murph Capers, Jr., Argyle, TX (US)

(72) Inventors: Seth Jared Capers, Argyle, TX (US); Seth Murph Capers, Jr., Argyle, TX (US)

(*) Notice: Subject to any disclaimer, the term of this patent is extended or adjusted under 35 U.S.C. 154(b) by 39 days.

(21) Appl. No.: 13/999,816

(22) Filed: Mar. 24, 2014

(65) Prior Publication Data

US 2014/0289937 A1 Oct. 2, 2014

Related U.S. Application Data

(60) Provisional application No. 61/853,007, filed on Mar. 26, 2013.

(51) Int. Cl.
*A61F 9/02* (2006.01)
*A42B 3/26* (2006.01)

(52) U.S. Cl.
CPC .. *A61F 9/025* (2013.01); *A42B 3/26* (2013.01)

(58) Field of Classification Search
CPC ........... A61F 9/022; A61F 9/025; A42B 3/26; A42B 3/24
USPC ...................................... 2/424, 434, 441, 443
See application file for complete search history.

(56) References Cited

U.S. PATENT DOCUMENTS

| | | | | |
|---|---|---|---|---|
| 2,511,329 A * | 6/1950 | Craig | ............... | 351/47 |
| 2,901,750 A * | 9/1959 | McMurry | ........... | 2/415 |
| 4,076,373 A * | 2/1978 | Moretti | ............ | 359/507 |
| 4,138,746 A * | 2/1979 | Bergmann | ......... | 2/424 |
| 4,455,689 A * | 6/1984 | Boyer | ................ | 2/434 |
| 4,547,909 A * | 10/1985 | Bell | ................... | 2/431 |
| 4,563,065 A * | 1/1986 | Kreissl | ............. | 351/86 |
| 4,716,601 A | 1/1988 | McNeal | | |
| 5,592,698 A * | 1/1997 | Woods | .............. | 2/424 |
| 5,671,483 A * | 9/1997 | Reuber | ............. | 2/424 |
| 5,809,580 A * | 9/1998 | Arnette | ............ | 2/426 |
| D407,735 S * | 4/1999 | Arnette | ........... | D16/312 |
| 6,085,358 A * | 7/2000 | Cogan | .............. | 2/424 |
| 6,388,813 B1 * | 5/2002 | Wilson et al. | ............... | 359/630 |
| 6,463,590 B1 * | 10/2002 | Dean et al. | ................. | 2/15 |
| 6,536,045 B1 * | 3/2003 | Wilson et al. | ................ | 2/15 |
| 6,847,492 B2 * | 1/2005 | Wilson et al. | ............... | 359/642 |
| 6,870,686 B2 * | 3/2005 | Wilson et al. | ............... | 359/642 |
| 7,184,217 B2 * | 2/2007 | Wilson et al. | ............... | 359/630 |
| 7,540,039 B2 * | 6/2009 | Reaux | .............. | 2/424 |
| 7,629,052 B2 * | 12/2009 | Brumwell | .............. | 428/426 |
| 8,088,462 B1 * | 1/2012 | Cockman et al. | ........... | 428/40.1 |
| 8,261,375 B1 * | 9/2012 | Reaux | .............. | 2/424 |
| 8,277,916 B2 * | 10/2012 | Cockman et al. | ........... | 428/40.1 |
| 8,407,818 B2 * | 4/2013 | VanDerWoude et al. | ........ | 2/424 |
| 8,693,102 B2 * | 4/2014 | Wilson et al. | ............... | 359/630 |

* cited by examiner

*Primary Examiner* — Danny Worrell
(74) *Attorney, Agent, or Firm* — Laura G. Barrow

(57) ABSTRACT

A novel removable lens strip system suitable for use with goggles and helmets is disclosed, wherein lens strips may be easily removed from the goggle lens or helmet shield as the strips become soiled, and thus obstructing the user's vision. More specifically, a guide piece is employed that shields underlying removable lens strips from being inadvertently removed.

22 Claims, 6 Drawing Sheets

# GUIDE FOR TEAR-OFF EYEWEAR LENS STRIPS

BACKGROUND AND SUMMARY OF THE INVENTION

This application claims the benefit of the filing of U.S. provisional application Ser. No. 61/853,007 filed Mar. 26, 2013, and which is incorporated by reference herein in its entirety.

The present invention is directed to a removable lens strip system suitable for use with protective eyewear or helmet. The inventive system is particularly suitable for use with motorcycle goggles or helmets, wherein the lens or helmet shield will get dirty with mud and debris, thereby reducing visibility and thus causing a danger to the rider. The present invention is also directed to a method of preventing the inadvertent removable of multiple removable lens strips.

Specifically, the system comprises a tear-off guide piece for use with protective eyewear, such as goggles and helmet shields. Currently for off-road motorcycle and all terrain vehicle use, it is common for riders to use a clear removable tear-off lens system secured to the goggles lens, as illustrated and described in U.S. Pat. No. 4,716,601 to McNeal (hereinafter '601 patent), which is incorporated herein by reference in its entirety. As shown in FIG. 2, conventional tear-off systems for goggle lens 4 (such as those described in the '601 patent, for example), comprise a top tear off lens strip 5 and one or more additional tear-off lens strips secured beneath the top tear-off lens strip, with the final tear off lens strip (i.e. the inner-most strip 6) secured directly onto the surface of the goggle lens 4. The tear-off strips are typically secured to the lens by means of tear-off securing posts 9. The elongated tear-off tabs 8 may also be secured via a second tear off securing post 10. The additional tear-off tabs 8 are folded underneath the top tear off tab. This system provides the rider clear vision by enabling the rider to remove the top clear tear off lens strip when it has become covered with dirt, mud, or debris. When the top tear off strip is pulled and removed via an extended top tear off tab 7, the additional tear off tab 8 on the next tear off lens strip extends to become the new top tear off lens strip on the goggles lens. The top tear off is removed by the rider by grasping with the thumb and forefinger 12 and pulling forward. The rider must use care to grab only the top tear-off lens strip, however. If the additional tear off strips are grabbed, then multiple tear off lens strips may be pulled inadvertently, leaving the rider with fewer, or no, additional tear off lens strips with which to clear vision.

In order to prevent the inadvertent removal of underlying tear-off strips, the current invention includes a tear off guide piece 11 which provides a means to shield the folded over underlying tear off strips and guide the rider's hand 12 to the top-most tear off lens strip tab 7, thus preventing the additional tear off lens strip tabs from being pulled inadvertently.

As discussed in more detail below, certain aspects of the present invention are directed to a removable lens strip tear-off system suitable for use with goggles and headwear shields and comprises a stack of at least two removable lens strips secured next to one another by at least one securing post. The stack includes a top-most strip and an inner-most strip, wherein the inner most strip is secured directly to a top surface of the eyewear lens system. Each of the strips has an extended tab configured to allow the user to remove the top-most strip from the stack. Each of the extended tabs of the strips underlying the top-most strip are folded upon itself and not fully extended until becoming the top-most strip. The inventive system further includes a guide piece positioned adjacent to a securing post to create a space therebetween wherein the underlying extended tabs are housed. As a result of this arrangement, the guide piece is positioned near the extended tab of the inner most strip, such that the inner-most strip tab is shielded by the guide piece. As the user grabs the tab of the top-most lens strip, the guide piece prevents the user from removing underlying lens strips as the user's hand, generally the thumb, comes in contact with the guide piece.

In other aspects of the invention, the eyewear system may comprise goggles having either a strap for attachment to the user's helmet or head as well as eye lens upon which the stack of removable strips are secured. The guide piece may be secured to the strap. In other embodiments, the goggles may include a pair of ear pieces, with the guide piece secured to one of the ear pieces.

In other aspects of the invention, the guide piece includes an elongated platform subjacent the innermost elongated tab and a post integral with, and extending from, the platform, wherein the elongated tabs of the removable lens strips are secured to the post. In this embodiment, the guide piece platform may be secured to the goggle frames or to the goggle strap or helmet.

The present invention is also directed to a method for preventing the inadvertent removal of multiple lens strips from eyewear lens. Specifically, the method includes the steps of attaching a stack of removable lens strips to an eyewear lens. In this step, the stack comprises at least two removable lens strips which are secured to the eyewear lens system one another by at least one securing post. The stack of lens strips includes a top-most strip and an inner-most strip, wherein the inner-most strip is secured directly to the top surface of the eyewear lens. Each of the strips further includes an extended tab configured to allow a user to remove the top-most strip from the stack. Second, the method includes the step of attaching a guide piece near the stack of tear-off strips such that the guide piece is positioned adjacent to the securing post and near the extended tab of the inner-most strip. As shown in the figures, the securing post and guide post are positioned such that a space is created therebetween to house the extended strip tabs. Next, the method comprises removing only the top-most lens strip from the stack by securing, with a thumb and finger, an extended tab of the top-most lens strip, the guide piece shielding the thumb and finger from grasping tabs of the underlying lens strips until such underlying lens strips become a top-most lens strip.

In the inventive method, the eyewear system may comprise goggles, the goggles including one or more eye lens upon which the stack of removable strips are secured and a strap for attachment to the user's helmet or head. In this method, the guide piece may be secured to the goggles strap, to the goggles frame, or to the helmet. The guide piece in this method may alternatively include an elongated platform subjacent the inner-most elongated tab and a post integral with, and extending from, the platform, and wherein the elongated tabs of the removable lens strips are secured to the post. The platform may be secured to the goggles frames, to the goggles strap, or to the helmet.

DESCRIPTION OF THE EMBODIMENTS

Figure 1:
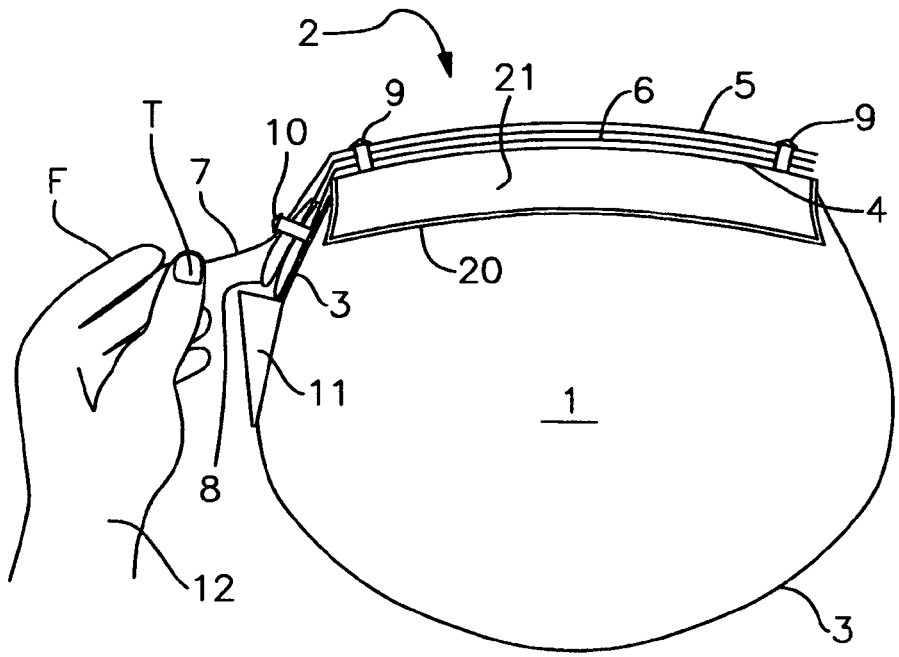
FIG. 1 is a top view of one embodiment of the inventive system, showing the guide piece secured to a goggle strap.
Figure 2:
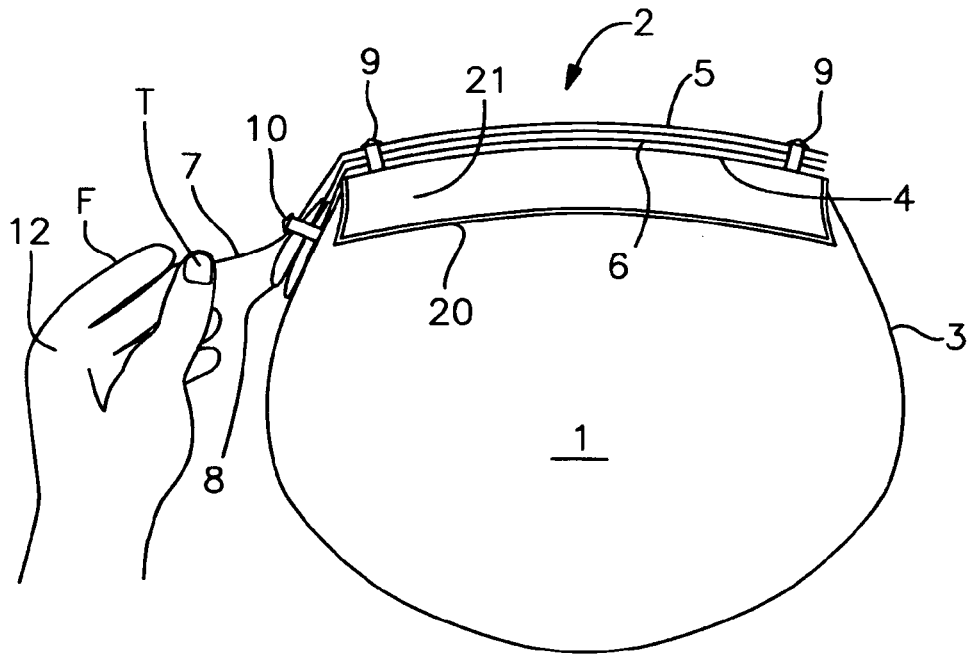
FIG. 2 is a top view of prior art lens strip tear-off system.

Referring now to the figures, FIG. 1 illustrates a first embodiment of the present invention. FIG. 1 is a top view of an eyewear system, namely a set of goggles 2 attached to a helmet 1. Attached to the goggle strap 3 is a guide piece 11. The guide piece 11 is positioned near the elongated tabs 7,8, thus shielding the underlying folded over tabs 8. FIG. 1 illustrates the user's hand 12 positioned above the guide piece 11 after securing the elongated tab 7 of the upper-most lens strip 5 with the thumb T and finger F. As shown, the guide piece 11 prevents the user's hand, and more generally the user's thumb T and finger F, from grabbing the underlying folded elongated tabs, such that only the upper-most lens strip 5 is removed from the goggles lens. The height B (see also FIG. 5) is configured such that only the top-most tab 7 is available for grasping.

Figure 5:
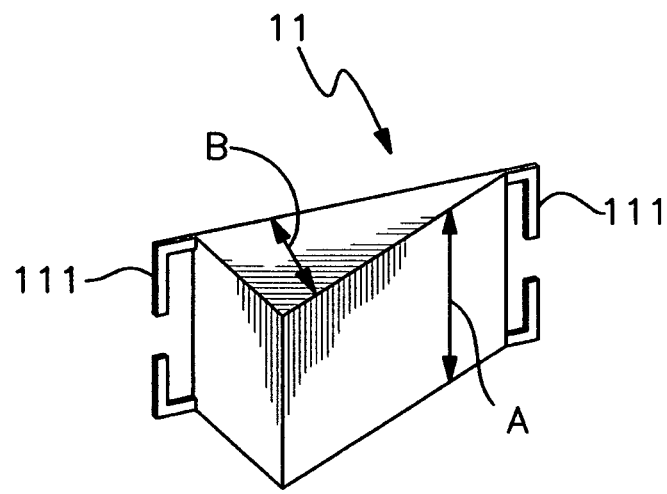
FIG. 5 is a perspective view of the inventive guide piece shown in FIG. 1.

FIG. 5 illustrates the embodiment of the guide piece as shown in FIG. 1. In this embodiment, the guide piece 11 has a pair of clips 111 configured to secure the goggle strap 3. It will be appreciated by those of ordinary skill in the art that the shape (wedge-shaped or non-wedge-shaped) and dimensions A,B of the guide piece as well as the configuration of the clips 111 may be modified, for example. The guide piece may also be fabricated by conventional materials, including but not limited to, metals, metal alloys, and plastic. The guide piece 11 could contain adjustments for both its width A and height B to accommodate a variety of goggle strap widths and additional tear-off strip quantities respectively, as illustrated in FIG. 5. Moreover, the guide piece 11 may omit the clips 111 and instead, employ any other attachment means known in the art. Exemplary attachment means may include, but are not limited to, any variety of temporary or permanent affixing adhesives, snaps, VELCRO (i.e. hook and loop fasteners), threaded fasteners, and the like.

While FIG. 1 illustrates the guide piece 11 secured to the goggle strap, it will be appreciated by the skilled artisan that the guide piece may be employed with any variety of protective eyewear, including eyewear secured to the user's head via ear pieces, as opposed to a strap (not shown). In such uses, the guide piece 11 may be fastened by any convention means to an ear piece.

Figure 3:
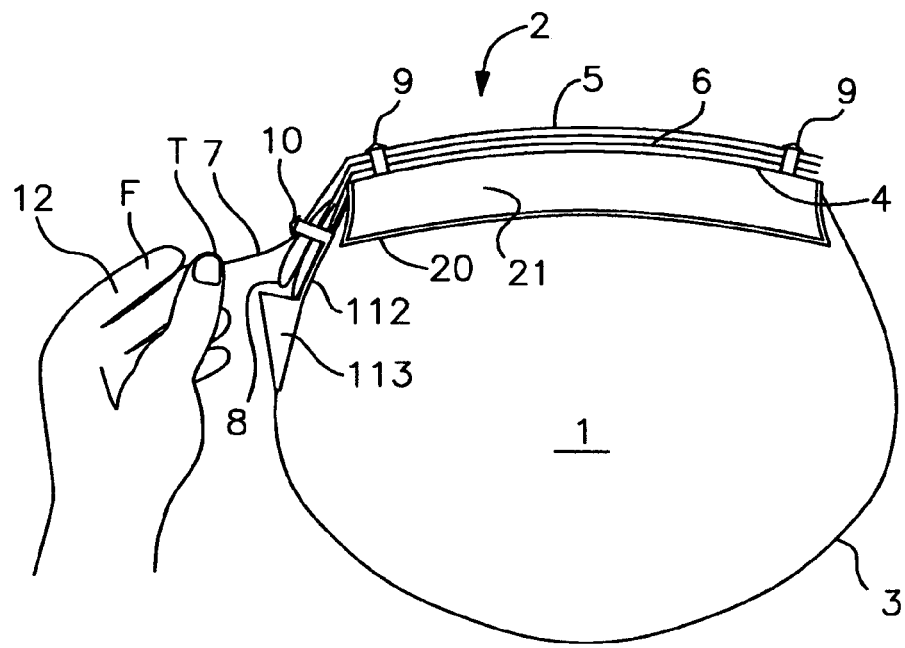
FIG. 3 is a top view of a second embodiment of the inventive system, showing the guide piece as an integral part of the securing post for the lens strip tabs.
Figure 6:
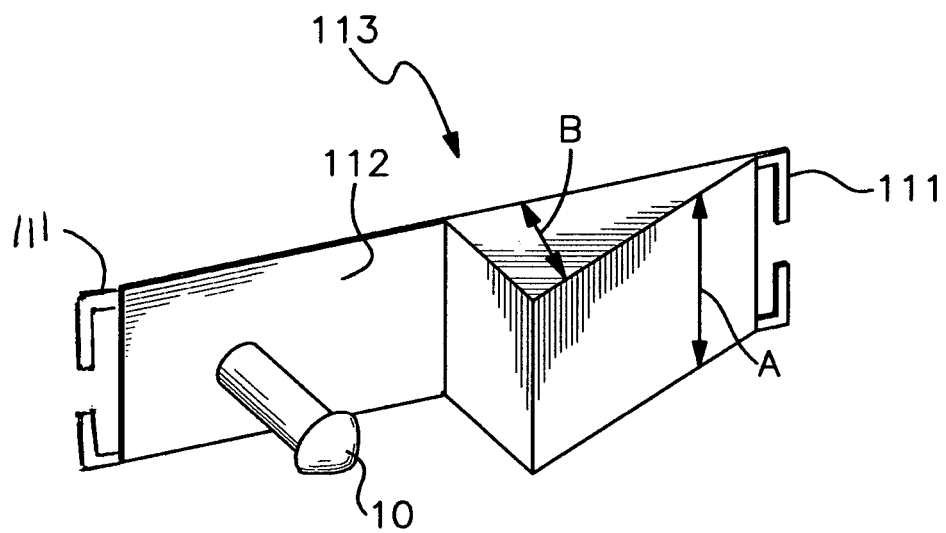
FIG. 6 is a perspective view of the inventive guide piece shown in FIG. 3.

FIGS. 3 and 6 illustrate another embodiment of the inventive guide piece, wherein the guide piece 113 includes an elongated platform 112 integral with a tear-off securing post 10. Again, the length and configuration of the guide piece 113 and platform 112 may be modified as desired. In this embodiment, the platform 112 is secured directly to the strap 3. As discussed above, if eyewear includes ear pieces as opposed to a strap, the guide piece may be secured to the ear piece.

Figure 4:
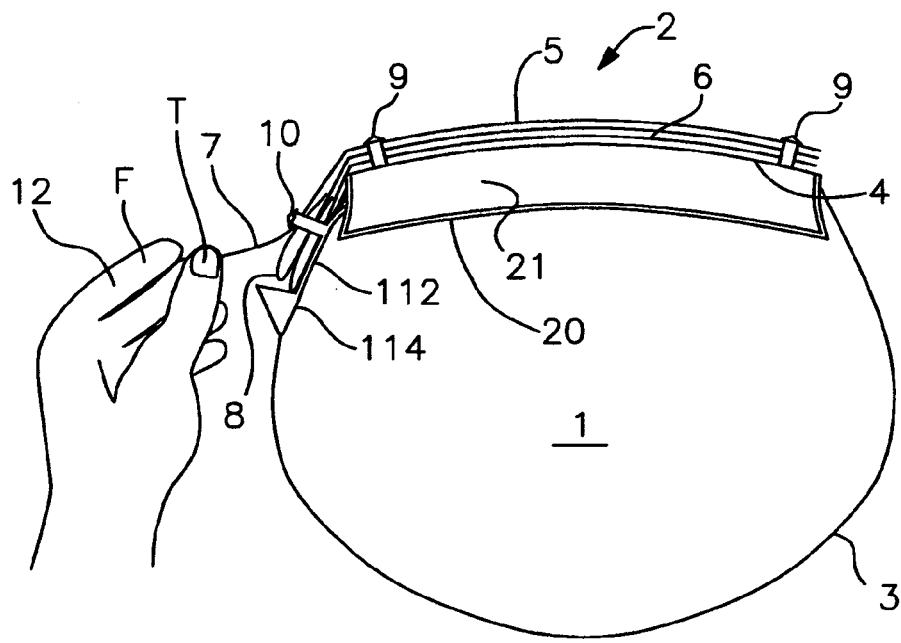
FIG. 4 is a top view of a third embodiment of the inventive system, showing the guide piece as an integral part of the securing post for the lens strip tabs and further secured to the frame of the goggles.
Figure 7:
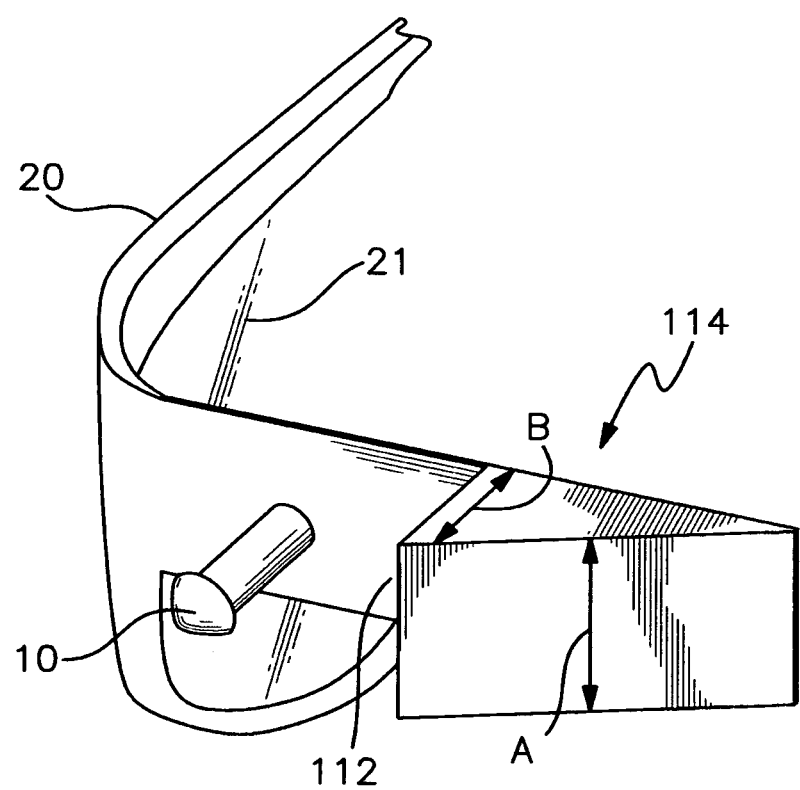
FIG. 7 is a perspective view of the inventive guide piece shown in FIG. 4.

FIGS. 4 and 7 illustrate a third embodiment of the inventive guide piece 114, similar to that shown in FIGS. 3 and 6, but wherein the platform 112 is integral with the frame 20 of the goggles.

All of the figures illustrate the guide piece 11, 113, 114 as having a wedge configuration; however, as discussed above, the guide piece can have any configuration, provided that it is sized and positioned to shield the elongated tabs 8 from inadvertent removal by the user until the tabs 8 becoming the top-most tab 7.

In addition, the tear-off system illustrated herein for use with the inventive guide piece and method as well as the system described in the '601 patent, as discussed above, are only exemplary tear-off systems. The size and configuration of such tear-off systems may be modified and still be within the scope of the present invention, provided such systems include a stack of tear-off lens strips having elongated tabs used for removal of each tear-off lens strip.

The present invention has been illustrated and described herein with respect to its use with goggles. The goggles shown in FIGS. 1-4 are conventional goggles having lens 4 housed within a frame 20; however, it will be recognized by those of ordinary skill in the art that the invention is not limited to conventional goggles, and thus, it may be employed with any type of protective eyewear.

Figure 8:
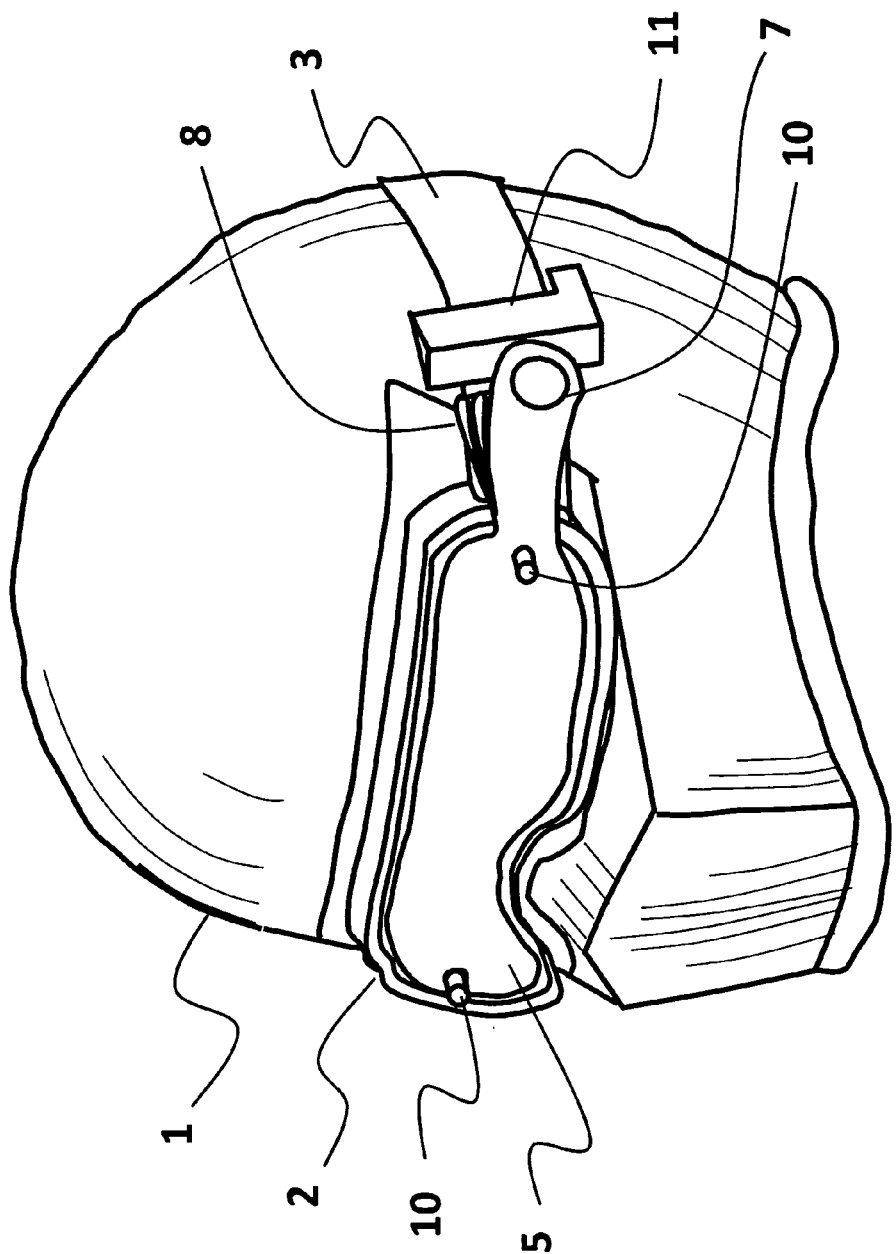
FIG. 8 is a perspective view of the inventive system in use with goggles, wherein the guide piece is attached directly to the helmet.
Figure 9:
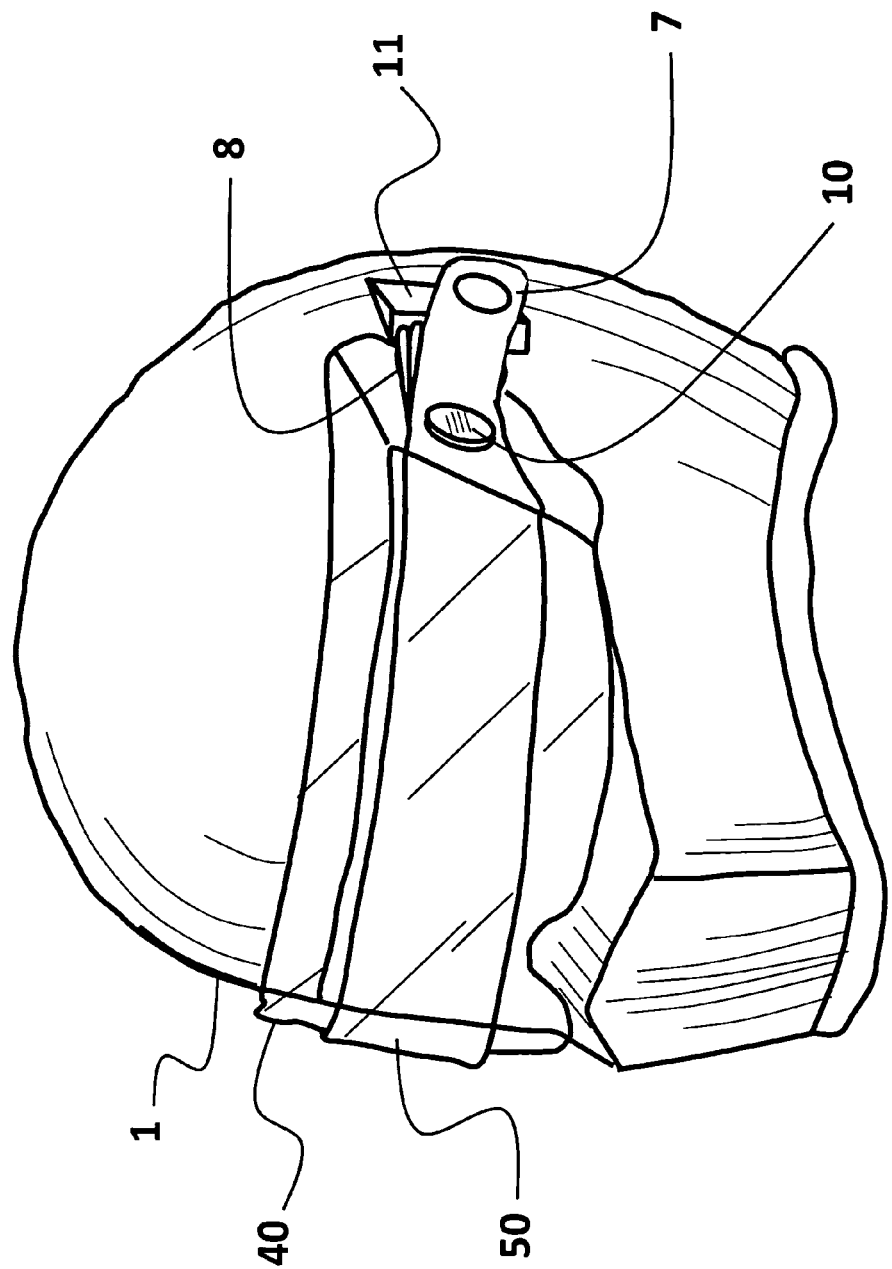
FIG. 9 is a perspective view of the inventive system in use with the helmet shield, wherein the guide piece is attached directly to the helmet.

Moreover, as shown in FIG. 8, the inventive guide piece 11 may also be secured directly to the user's headwear, such as a helmet 1 (as opposed to the goggles strap), and positioned near the elongated tab portions 7,8 of the tear-off lens strips as discussed above. As shown in FIG. 9, the guide piece 11 could also be used in conjunction with larger helmet shield tear-off strips 50, wherein the guide piece would be affixed to the outside of the helmet 1 to shield the elongated tabs 7,8 extending from the tear-off strips 50 of the helmet shield 40 from inadvertent removal by the user.

The invention claimed is:

1. A removable lens strip tear-off system suitable for use with goggles and headwear shields, said system comprising:
   a. a stack of at least two removable lens strips secured next to one another, said stack comprising a top-most strip and an inner most strip, said inner most strip secured directly to a top surface of an eyewear lens system;
   b. at least one securing post, wherein said removable lens strips are secured to said eyewear system by said at least one securing post;
   c. each of said strips having an extended tab configured to allow a user to remove said top-most strip from said stack, wherein each of the tabs of the strips underlying said top-most strip are folded upon itself and not fully extended until becoming the top-most strip; and
   d. a guide piece configured for attachment near said stack of tear-off strips, wherein said guide piece is positioned adjacent to said at least one securing post to form a space therebetween, such that said extended tabs of said innermost and underlying strips are housed within said space and shielded by said guide piece
   whereby as a user grabs the tab of said top-most strip, said guide piece prevents the user from removing underlying lens strips as said user's hand comes in contact with said guide piece.

2. The tear-off system of claim 1, wherein said eyewear system comprises goggles, said goggles further comprising one or more eye lens upon which said stack of removable lens strips are secured and a strap for attachment to a user's helmet or head.

3. The tear-off system of claim 2, wherein said guide piece is secured to said strap.

4. The tear-off system of claim 2, said goggles further including a frame housing said eye lens, and wherein said guide piece is secured to said frame.

5. The tear-off system of claim 1, said tear-off system further including an elongated platform connected to said guide piece and said at least one securing post.

6. The tear-off system of claim 5, wherein said platform of said guide piece is secured to said frame of said goggles.

7. The tear-off system of claim 5, wherein said platform of said guide piece is secured to said strap.

8. The tear-off system of claim 1, said eyewear system comprising a helmet shield upon which said stack of removable lens strips are secured, and wherein said guide piece is secured to said user's helmet.

9. A method for preventing the inadvertent removal of multiple lens strips from eyewear lens, said method comprising the steps of:
 a) attaching a stack of removable lens strips to an eyewear lens, said stack comprising at least two removable lens strips secured next to one another by at least one securing post, said stack further comprising a top-most strip and an inner most strip, said inner most strip secured directly to a top surface of said eyewear lens; each of said strips having an extended tab configured to allow a user to remove said top-most strip from said stack;
 b) attaching a guide piece near said extended tabs of said innermost and underlying strips such that said guide piece is positioned adjacent said securing post to form a space between said guide piece and said securing post, such that said extended tabs of said innermost and underlying strips are housed within said space; and
 c) removing only the top-most lens strip from said stack by securing with a thumb and finger an extended tab of said top-most lens strip, said guide piece shielding said thumb and finger from grasping tabs of said underlying lens strips until such underlying lens strips become a top-most lens strip.

10. The method of claim 9, wherein said eyewear system comprises goggles, said goggles further comprising one or more eye lens upon which said stack of removable strips are secured and a strap for attachment to a user's helmet or head.

11. The method of claim 10, wherein said guide piece is secured to said strap.

12. The method of claim 10, said goggles further including a frame housing said eye lens, and wherein said guide piece is secured to said frame.

13. The method of claim 9, said tear-off system further including an elongated platform connected to said guide piece and said at least one securing post.

14. The method of claim 13, wherein said platform of said guide piece is secured to said frame of said goggles.

15. The method of claim 13, wherein said platform of said guide piece is secured to said strap.

16. The method of claim 9, said eyewear system comprising a helmet shield upon which said stack of removable lens strips are secured, and wherein said guide piece is secured to a helmet.

17. The tear-off system of claim 8, said tear-off system further including an elongated platform connected to said guide piece and said at least one securing post.

18. The method of claim 16, said tear-off system further including an elongated platform connected to said guide piece and said at least one securing post.

19. The tear-off system of claim 1, wherein said eyewear system comprises goggles attached to a helmet, said goggles further comprising one or more eye lens upon which said stack of removable lens strips are secured.

20. The tear-off system of claim 19, wherein said guide piece is secured to said helmet.

21. The method of claim 9, wherein said eyewear system comprises goggles attached to a helmet, said goggles further comprising one or more eye lens upon which said stack of removable strips are secured.

22. The method of claim 21, wherein said guide piece is secured to said helmet.

\* \* \* \* \*